(12) United States Patent
Nakanishi et al.

(10) Patent No.: US 10,945,683 B2
(45) Date of Patent: Mar. 16, 2021

(54) X-RAY COMPUTED TOMOGRAPHY APPARATUS

(71) Applicant: Toshiba Medical Systems Corporation, Otawara (JP)

(72) Inventors: Satoru Nakanishi, Utsunomiya (JP); Shuya Nambu, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 385 days.

(21) Appl. No.: 15/801,476

(22) Filed: Nov. 2, 2017

(65) Prior Publication Data

US 2018/0132799 A1 May 17, 2018

(30) Foreign Application Priority Data

Nov. 15, 2016 (JP) .............................. JP2016-222301

(51) Int. Cl.
*A61B 6/03* (2006.01)
*A61B 6/00* (2006.01)

(52) U.S. Cl.
CPC ............ *A61B 6/032* (2013.01); *A61B 6/5205* (2013.01); *A61B 6/5235* (2013.01); *A61B 6/5258* (2013.01); *A61B 6/542* (2013.01); *A61B 6/545* (2013.01); *A61B 6/465* (2013.01)

(58) Field of Classification Search
None
See application file for complete search history.

(56) References Cited

U.S. PATENT DOCUMENTS

| | | | |
|---|---|---|---|
| 6,438,195 B1 * | 8/2002 | Hsieh | G06T 5/50 378/4 |
| 6,459,755 B1 * | 10/2002 | Li | A61B 6/032 378/4 |
| 2003/0169847 A1 * | 9/2003 | Karellas | A61B 6/482 378/98.3 |

(Continued)

FOREIGN PATENT DOCUMENTS

| | | |
|---|---|---|
| JP | H09-56712 A | 3/1997 |
| JP | 2004-522508 | 7/2004 |

(Continued)

OTHER PUBLICATIONS

Japanese Office Action dated Jul. 7, 2020, issued in Japanese Patent Application No. 2016-222301.

(Continued)

*Primary Examiner* — Edwin C Gunberg
(74) *Attorney, Agent, or Firm* — Oblon, McClelland, Maier & Neustadt, L.L.P.

(57) ABSTRACT

According to one embodiment, an X-ray computed tomography apparatus includes processing circuitry. The processing circuitry sets a parameter of an examination protocol. Based on the set parameter, the processing circuitry determines the number of acquisition views and the number of reconstruction views of projection data. The processing circuitry acquires first projection data corresponding to the number of acquisition views. The processing circuitry calculates second projection data corresponding to the number of reconstruction views based on the first projection data. The processing circuitry reconstructs a CT image based on the second projection data.

10 Claims, 4 Drawing Sheets

(56) References Cited

U.S. PATENT DOCUMENTS

2007/0036265 A1* 2/2007 Jing ................. A61B 6/4417
378/37

FOREIGN PATENT DOCUMENTS

| JP | 2013-000479 | 1/2013 |
| JP | 2014-014418 A | 1/2014 |
| JP | 2015-208601 | 11/2015 |
| WO | WO 2016/080311 A1 | 5/2016 |

OTHER PUBLICATIONS

Japanese Office Action dated Nov. 4, 2020, issued in Japanese Patent Application No. 2016-222301.

* cited by examiner

3200 views = View number (moire artifact disappears at FOV=500mm)

| Examination protocol | Acquisition view number | Reconstruction view number | Interpolation view number |
|---|---|---|---|
| FOV=320mm | 1800 | 3200 | 1400 |
| FOV=500mm Low dosage | 2500 | 3200 | 700 |
| FOV=500mm Perfusion | 1500 | 3200 | 1700 |
| FOV=500mm Iterative reconstruction | 2600 | 3200 | 600 |

| Rotation speed (s/rot) | Acquisition view number (Normal resolution mode) | Acquisition view number (High resolution mode) | Acquisition view number (High resolution + low dose mode) |
|---|---|---|---|
| 0.3 | 800 | 1000 | 900 |
| 0.5 | 1000 | 1300 | 1200 |
| 1 | 1500 | 1800 | 1600 |
| 1.5 | 2000 | 2400 | 2200 |

FIG. 7

X-RAY COMPUTED TOMOGRAPHY APPARATUS

CROSS-REFERENCE TO RELATED APPLICATIONS

This application is based upon and claims the benefit of priority from the prior Japanese Patent Application No. 2016-222301, filed Nov. 15, 2016, the entire contents of which are incorporated herein by reference.

FIELD

Embodiments described herein relate generally to an X-ray computed tomography apparatus.

BACKGROUND

In the case of acquiring data by high-speed rotation in an X-ray computed tomography apparatus including a high-resolution detector, since the view rate (the number of views per unit of time) of current data acquisition circuitry is insufficient, a moire artifact (interference pattern) appears around a field of view (FOV) in a reconstructed image. By increasing the number of views per unit of time through hardware, the moire artifact will decrease. However, since the number of incident photons per view will also decrease relatively, a noise artifact will appear instead of the moire artifact. On the other hand, if the number of views is increased through software, such as by view interpolation, although the moire artifact will decrease, an artifact that flows in a rotational direction will appear.

DETAILED DESCRIPTION

An X-ray computed tomography apparatus according to the present embodiment includes processing circuitry. The processing circuitry sets a parameter of an examination protocol. Based on the set parameter, the processing circuitry determines the number of acquisition views and the number of reconstruction views of projection data. The processing circuitry acquires first projection data corresponding to the number of acquisition views. The processing circuitry calculates second projection data corresponding to the number of reconstruction views based on the first projection data. Based on the second projection data, the processing circuitry reconstructs a CT image.

In the following, the X-ray computed tomography apparatus according to the present embodiment will be explained with reference to the drawings.

Figure 1:
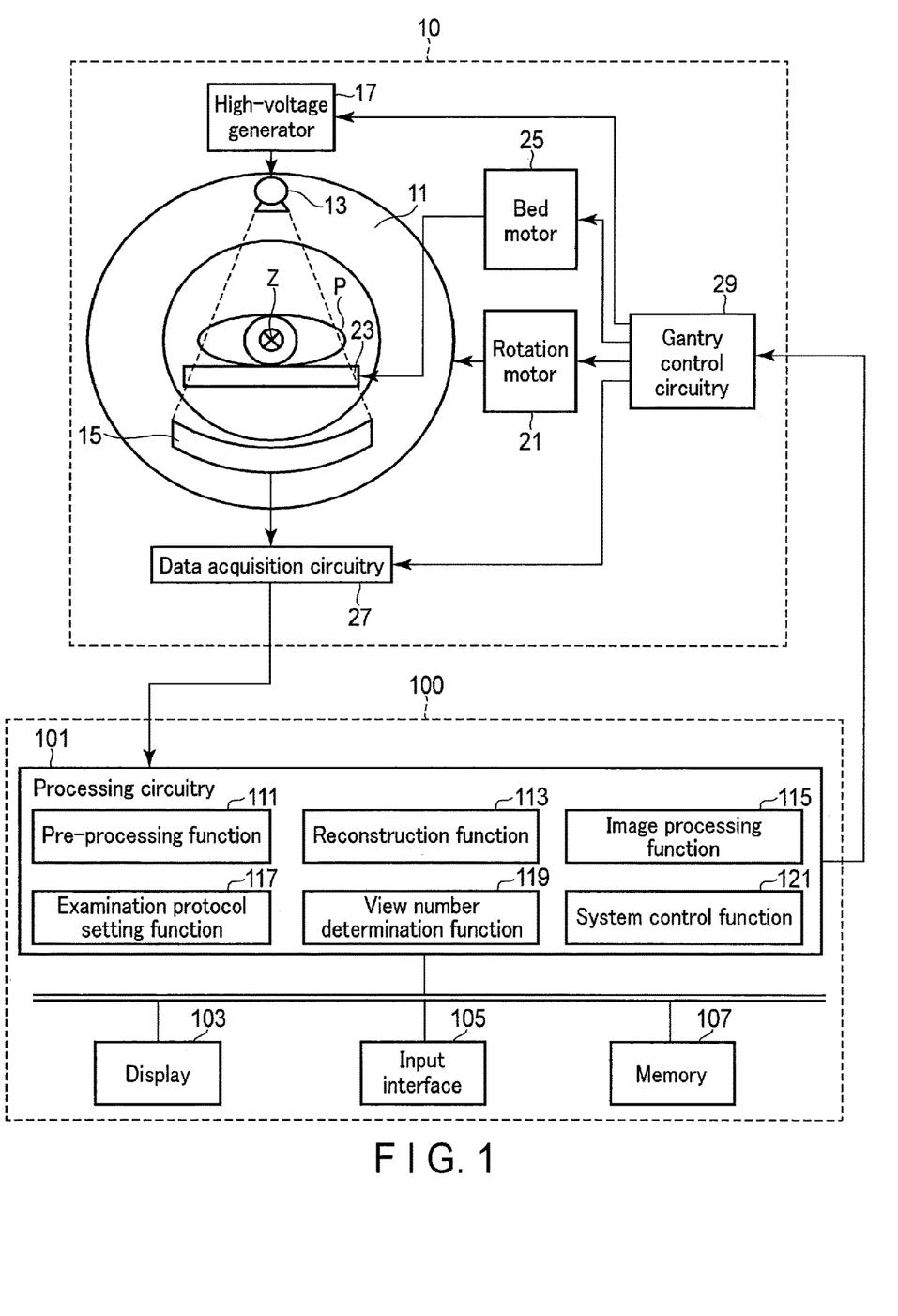
FIG. 1 is a view showing a configuration of an X-ray computed tomography apparatus according to a present embodiment.

FIG. 1 is a view showing a configuration of the X-ray computed tomography apparatus according to the present embodiment. As shown in FIG. 1, the X-ray computed tomography apparatus of the present embodiment includes a gantry 10 and a console 100. For example, the gantry 10 is installed in a CT examination room, and the console 100 is installed in a control room adjacent to the CT examination room. The gantry 10 and the console 100 are communicatably connected to each other. The gantry 10 includes a scan mechanism configured to perform X-ray CT scan of a subject P. The console 100 is a computer that controls the gantry 10.

As shown in FIG. 1, the gantry 10 includes an almost cylindrical rotation frame 11 with a bore. As shown in FIG. 1, an x-ray tube 13 and an X-ray detector 15, which are arranged to face each other via the bore, are attached to the rotation frame 11. The rotation frame 11 is a metal frame made of a metal, such as aluminum, into an annular shape. As will be explained in detail later on, the gantry 10 includes a main frame made of metal, such as aluminum. The rotation frame 11 is rotatably supported by the main frame.

The X-ray tube 13 is connected to a high-voltage generator 17. The X-ray tube 13 is a vacuum tube with a cathode that generates thermoelectrons and an anode that generates X-rays by receiving the thermoelectrons emitted from the cathode. The high-voltage generator 17 is attached to, for example, the rotation frame 11. The high-voltage generator 17 is, for example, inverter-type high-voltage generating circuitry. The high-voltage generator 17 generates a high voltage to be applied to the X-ray tube 13 from the power supplied from the power supply unit (not shown) of the gantry via the slip ring and the brush, and supplies a filament heating current under the control of gantry control circuitry 29. The high-voltage generator 17 and the X-ray tube 13 are connected via a high voltage cable (not shown). The high voltage generated by the high-voltage generator 17 is applied between an anode and a cathode stored in the X-ray tube 13 via the high voltage cable. The filament heating current generated by the high-voltage generator 17 is applied to the cathode of the X-ray tube 13 via the high voltage cable. The high voltage applied between the anode and the cathode of the X-ray tube 13 is called a tube voltage. A flow of thermoelectrons that is generated from the cathode heated by the filament heating current and flows to the anode under the high voltage is called a tube current. The high-voltage generator 17 adjusts the tube voltage and the tube current to be applied to the X-ray tube 13 in accordance with an X-ray condition.

The rotation frame 11 rotates about the center axis Z at a predetermined angular velocity upon receiving power from a rotation motor 21. As the rotation motor 21, a given motor, such as a direct drive motor or a servo motor, is used. The rotation motor 21 is stored in, for example, the gantry 10. Upon receiving a driving signal from the gantry control circuitry 29, the rotation motor 21 generates power to rotate the rotation frame 11.

An FOV is set in the bore of the rotation frame 11. A table top supported by a bed 23 is inserted into the bore of the rotation frame 11. The subject P is placed on the table top.

The bed 23 movably supports the table top. A bed motor 25 is stored in the bed 23. Upon receiving a driving signal from the gantry control circuitry 29, the bed motor 25 generates power to move the bed 23 in the longitudinal direction, the vertical direction, and the widthwise direction. The table top is positioned so that an imaging portion of the subject P placed thereon is included in the FOV.

The X-ray detector 15 detects the X-rays generated by the X-ray tube 13. Specifically, the X-ray detector 15 includes a plurality of detection elements arranged on a two-dimensional curved surface. Each of the detection elements includes a scintillator and a photoelectric conversion element. The scintillator is formed of a material that converts X-rays into light. The scintillator converts incident X-rays into the number of photons corresponding to the intensity of the incident X-rays. The photoelectric conversion element is a circuit element that amplifies light received from the scintillator and converts it into an electric signal. As the photoelectric conversion element, for example, a photomultiplier, a photodiode, or the like is used. The detection element may be an indirect detection type that converts X-rays into light and then detects the light, as described above, or a direct conversion type that directly converts X-rays into an electrical signal. As the detection element of the direct detection type, for example, a type including a semiconductor diode formed by attaching electrodes to both ends of a semiconductor, such as an SiPM (Silicon Photomultipliers), is applicable.

Figure 2:
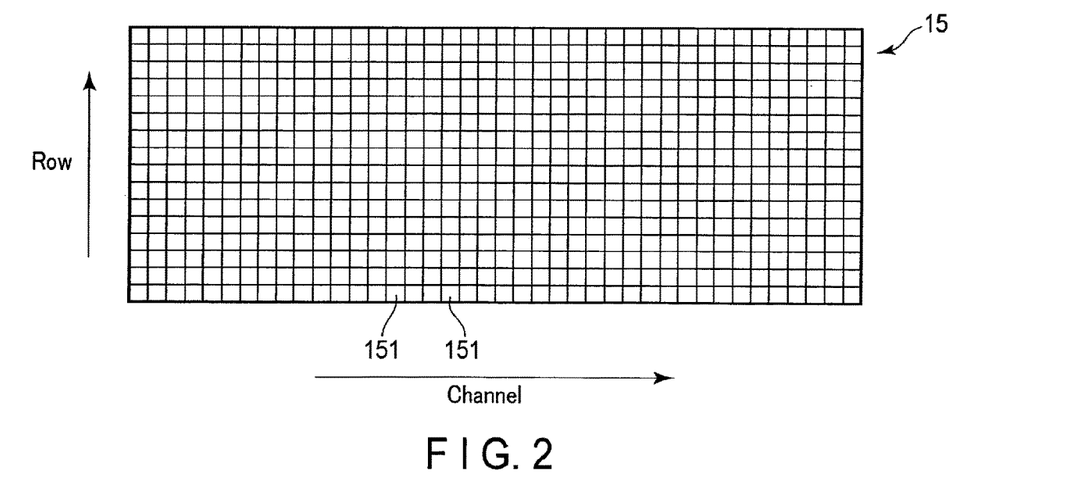
FIG. 2 is a plane view schematically showing an array of detection elements included in an X-ray detector according to the present embodiment.

FIG. 2 is a plane view schematically showing an array of detection elements 151 included in the X-ray detector 15 according to the present embodiment. As shown in FIG. 2, a plurality of detection elements 151 are arranged two-dimensionally in a channel direction and a row direction. The row direction is defined as a direction along a rotation axis Z, and the channel direction is defined as a rotational direction about the rotation axis Z of the X-ray detector 15. The X-ray detector 15 of the present embodiment includes a plurality of detection elements for high-resolution (hereinafter, referred to as high-resolution elements) 151.

The X-ray detector 15 of the present embodiment is capable of switching resolutions regarding the channel direction (hereinafter, referred to as detector resolution). Modes relating to the detector resolution may be categorized into a high-resolution mode or a normal resolution mode. As shown in FIG. 2, the high-resolution mode is an image quality mode in which the detector resolution in the channel direction corresponds to a pitch between the high-resolution elements 151. The normal resolution mode is an image quality mode in which the detector resolution regarding the channel direction corresponds to a pitch that is wider than the pitch between the high-resolution elements 151.

Figure 3:
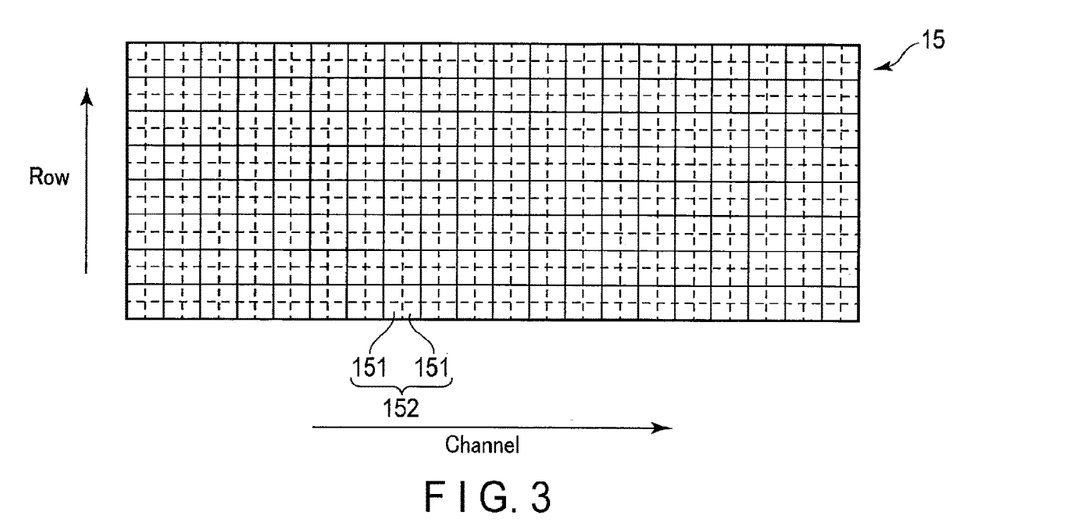
FIG. 3 is a plane view schematically showing an alignment of detection elements of the X-ray detector according to the present embodiment in a normal resolution mode.

The high-resolution mode and the normal resolution mode may be electrically switched by the gantry control circuitry 29, etc. FIG. 3 is a plane view schematically showing an alignment of detection elements 151 of the X-ray detector 15 in the normal resolution mode. As shown in FIG. 3, the normal resolution mode is achieved by electrically bundling the number of high-resolution elements 151 in accordance with the magnification of the resolution of the high-resolution with respect to the normal resolution. For example, in the case where the resolution of the high-resolution is four-times the normal resolution mode, a total of four pieces of high-resolution elements 151, obtained by two vertical pieces times two horizontal pieces, will configure one normal resolution mode detection element (hereinafter, normal resolution element) 152. Electric signals of four high-resolution elements 151 configuring the normal resolution element 152 will be bundled. The bundled electric signals will be processed as the electric signal of the normal resolution element 152. A normal resolution image can be reconfigured based on the electric signal from the normal resolution element 152. In the case of the high-resolution mode, by independently utilizing the electric signal from each of the high-resolution elements 151, a high-resolution image corresponding to the pitch between the high-resolution elements 151 can be reconfigured.

Data acquisition circuitry 27 is connected to the X-ray detector 15. The data acquisition circuitry 27 reads out from the X-ray detector 15 an electric signal corresponding to the intensity of X-rays detected by the X-ray detector 15, and acquires projection data having a digital value corresponding to the dose of X-rays during a view period. The data acquisition circuitry 27 is implemented by, for example, an ASIC (Application Specific Integrated Circuit) on which a circuit element that is capable of generating projection data is mounted.

The gantry control circuitry 29 controls the gantry 10 to carry out X-ray CT scanning in accordance with scan conditions made by processing circuitry 101 of the console 100. The gantry control circuitry 29 of the present embodiment synchronously controls the high-voltage generator 17, the rotation motor 21, the bed motor 25, and the data acquisition circuitry 27 to acquire projection data of the number of acquisition views determined by the processing circuitry 101 of the console 100. The number of acquisition views indicates the number of views of projection data acquired by the X-ray CT scanning. Specifically, the number of acquisition views is adjusted by at least one of adjusting the rotation speed of the rotation frame 11 of the gantry 10 by the rotation motor 21, and/or adjusting the view period by the data acquisition circuitry 27. As hardware resources, the gantry control circuitry 29 includes a processing device (processor) such as a CPU (Central Processing Unit) or an MPU (Micro Processing Unit), and a storage device (memory) such as a ROM (Read Only Memory) and a RAM (Random Access Memory). The gantry control circuitry 29 may be implemented by an ASIC or a FPGA (Field Programmable Gate Array), a CPLD (Complex Programmable Logic Device), or an SPLD (Simple Programmable Logic Device).

As shown in FIG. 1, the console 100 includes the processing circuitry 101, a display 103, input circuitry 105, and memory 107. Data communication between the processing circuitry 101, the display 103, the input circuitry 105, and the memory 107 is performed via a bus.

The processing circuitry 101 includes a processor, such as a CPU, an MPU, or a GPU (Graphics Processing Unit), and a memory, such as a ROM or a RAM, as hardware resources. The processing circuitry 101 executes various programs to implement a preprocessing function 111, a reconstruction function 113, an image processing function 115, an examination protocol setting function 117, a view number determination function 119, and a system control function 121.

In the preprocessing function 111, the processing circuitry 101 subjects raw data transmitted from the gantry 10 to preprocessing, such as logarithmic conversion. The processing circuitry 101 also computes projection data of the number of reconstruction views based on the acquired projection data of the number of acquisition views. The number of reconstruction views indicates the number of views of projection data subjected to reconstruction processing by the processing circuitry 101. In more detail, the number of reconstruction views is the number of views immediately before a back projection processing. The processing circuitry 101 computes the projection data of the number of reconstruction views by performing view interpolation to the projection data of the number of acquisition views.

In the reconstruction function 113, the processing circuitry 101 generates a CT image representing a space distribution of CT values relating to the subject P based on the projection data of the number of reconstruction views. As the image reconstruction algorithm, an existing image reconstruction algorithm, such as an FBP (Filtered Back Projection) method or an iterative reconstruction method, may be used.

In the image processing function 115, the processing circuitry 101 subjects the CT image reconstructed by the reconstruction function 113 to various image processing. For example, the processing circuitry 101 subjects the CT image to three-dimensional image processing, such as volume rendering, surface volume rendering, image value projection processing, MPR (Multi-Planer Reconstruction) processing, or CPR (Curved MPR) processing, to generate a display image.

In the examination protocol setting function 117, the processing circuitry 101 sets an examination protocol regarding a CT scan for the subject P in accordance with the instruction from a user via the input circuitry 105, or automatically. The examination protocol according to the present embodiment includes both a photographing protocol regarding the CT scan performed by the gantry 10, and a reconstruction protocol regarding image reconstruction performed by the reconstruction function 113.

In the view number determination function 119, the processing circuitry 101 determines the number of views of the projection data to be acquired by the gantry 10 (the acquisition view number) and the number of views of the projection data to be utilized by the reconstruction function 113 (the reconstruction view number) corresponding to the examination protocol set by the examination protocol setting function 117. Typically, the acquisition view number and the reconstruction view number are determined prior to executing the CT scan in accordance with the examination protocol set by the examination protocol setting function 117.

In the system control function 121, the processing circuitry 101 comprehensively controls the X-ray computed tomography apparatus according to the present embodiment. Specifically, the processing circuitry 101 reads out a control program stored in the memory 107 and installs it in a memory, and controls the respective units of the X-ray computed tomography apparatus in accordance with the control program.

The preprocessing function 111, the reconstruction function 113, the image processing function 115, the examination protocol setting function 117, the view number determination function 119, and the system control function 121 may be implemented by the processing circuitry 101 of a certain substrate, or may be implemented by the processing circuitry 101 over a plurality of substrates.

The display 103 displays various data, such as a two-dimensional CT image and a display image. As the display 103, for example, a CRT display, a liquid crystal display, an organic EL display, an LED display, a plasma display, or any other display known in this technical field may be used as appropriate.

The input circuitry 105 accepts various instructions from the user. Specifically, the input circuitry 105 includes an input device and input interface circuitry. The input device accepts various instructions from the user. As the input device, a keyboard, a mouse, or various switches etc. may be used. The input interface circuitry supplies an output signal from the input device to the processing circuitry 101 via a bus.

The memory 107 is a storage device, such as an HDD (hard disk drive), an SSD (solid state drive), and an integrated circuit memory, which stores various information. The memory 107 may also be a driving device, etc. which reads and writes various information to and from portable storage media, such as a CD-ROM drive, a DVD drive, and a flash memory. The memory 107 stores data of, for example, a CT image and a display image. Furthermore, the memory 107 stores a control program and the like according to the present embodiment.

In the following, an operation example of the X-ray computed tomography apparatus of the present embodiment will be explained.

The relationship between the number of views and an artifact will be explained. An artifact indicates a pseudo image component that shows up on a CT image. In the case where the reconstruction view number is small, a moire artifact (interference pattern) appears around the FOV of a reconstructed image. For example, the moire artifact appears due to an insufficient view rate (the number of views per unit of time). The insufficient view rate becomes significant in the case where, for example, data is acquired by high-speed rotation of the gantry 10 on which the X-ray detector 15 including high-resolution elements is mounted.

In order to reduce the moire artifact, the acquisition view number per unit of time may be increased. When the acquisition view number per rotation is increased, the moire artifact decreases; however, since the number of incident photons per view decreases relatively, a noise artifact appears instead. In other words, as the number of views increases under the same X-ray dose, the moire artifact decreases, and the noise artifact increases.

By increasing the number of views through software, such as by view interpolation, the moire artifact decreases. If the number of views per rotation is large, it is known that although the moire artifact around the FOV decreases, excessive view interpolation will cause artifacts flowing in the rotational direction to appear.

The processing circuitry 101 of the present embodiment adaptively determines the number of views in accordance with the examination protocol in order to generate a CT image in which the reduction of moire artifacts caused by an insufficient number of views and the reduction of noise artifacts caused by an insufficient number of incident photons are harmonized. In the following, the processing performed by the X-ray computed tomography apparatus under the control of a system control function 121 will be explained through Example 1 and Example 2.

Example 1

Figure 4:
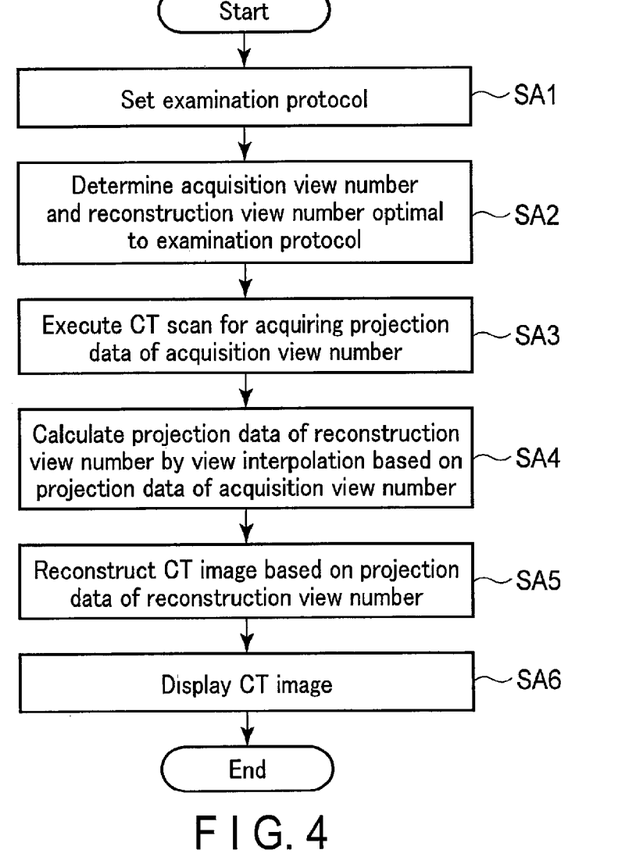
FIG. 4 is a view showing a typical flow of processing performed by the X-ray computed tomography apparatus under control of a system control function according to Example 1.

FIG. 4 is a view showing a typical flow of processing performed by the X-ray computed tomography apparatus under the control of the system control function 121 according to Example 1.

As shown in FIG. 4, the processing circuitry 101 first executes the examination protocol setting function 117 (step SA1). In step SA1, the processing circuitry 101 sets an examination protocol regarding a CT scan for a subject P in accordance with an instruction from a user via the input circuitry 105, or automatically. The examination protocol according to the present embodiment includes both a photographing protocol regarding the CT scan performed by the gantry 10, and a reconstruction protocol regarding image reconstruction performed by the reconstruction function 113.

Specifically, as a parameter configuring the examination protocol, a detector resolution of the X-ray detector 15 regarding the channel direction, a rotation speed, an FOV size, an image processing application, a reconstruction method, a reconstruction function, and an X-ray condition may be considered. The rotation speed is defined by the rotation speed of the rotation frame 11 about the Z-axis. The FOV size is defined by the length [mm] of the FOV regarding the radial direction. The image processing application is a kind of post-processing image application performed on a CT image. As the image processing application, for example, perfusion analysis may be considered. For example, the reconstruction method may be largely divided into an iterative reconstruction method and a reconstruction method that does not use the iterative reconstruction method. As the reconstruction method that does not use the iterative reconstruction method, for example, an analytical image reconstruction method, such as an FBP (filtered back projection) may be considered. The reconstruction function is a function, such as a filter function, that is used for the analytical image reconstruction method. The X-ray condition is defined by at least one parameter of, for example, a tube voltage, a tube current, or a tube current-time lapse product. The X-ray condition may also be expressed as a high dose or a low dose instead of a parameter.

After step SA1, the processing circuitry 101 executes the view number determination function 119 (step SA2). In step SA2, the processing circuitry 101 determines the acquisition view number and the reconstruction view number corresponding to the examination protocol set by the examination protocol setting function 117. The processing circuitry 101 determines the acquisition view number and the reconstruction view number corresponding to the examination protocol set in step SA1 based on an integrated evaluation of a pseudo image component caused by the insufficient acquisition view number per unit of time (that is, the moire artifact), a pseudo image component caused by the insufficient number of incident photons per acquisition view (that is, the noise artifact), and a pseudo image component caused by the view number increase process from the acquisition view number to the reconstruction view number (that is, an artifact caused by view interpolation, which flows in the rotational direction). For example, the processing circuitry 101 determines the acquisition view number and the reconstruction view number by using an LUT (look up table) that associates the acquisition view number with the reconstruction view number per examination protocol. Hereinafter, the LUT will be referred to as a first view number table. The first view number table is, for example, stored in the memory 107.

Figure 5:
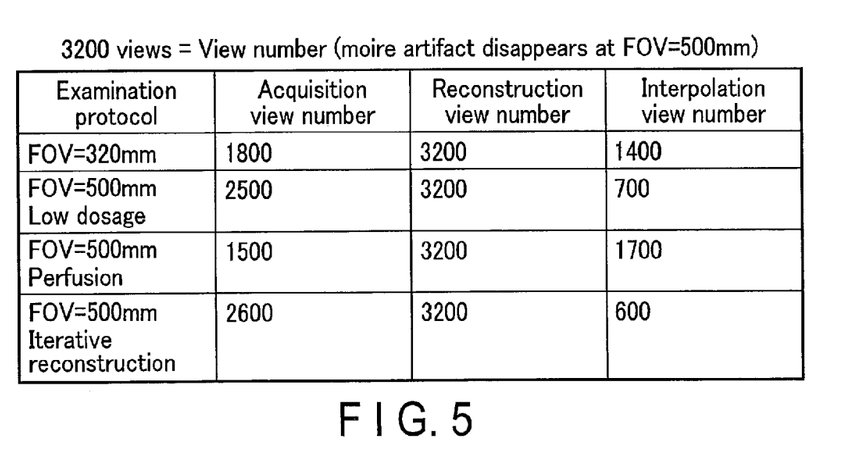
FIG. 5 shows an example of a first view number table utilized by processing circuitry in step SA2 of FIG. 4.

FIG. 5 shows an example of the first view number table utilized by the processing circuitry 101 in step SA2. As shown in FIG. 5, the first view number table associates the acquisition view number with the reconstruction view number per examination protocol. The first view number table may also have the interpolation view number associated per examination protocol. The interpolation view number is equivalent to the number obtained by subtracting the acquisition view number from the reconstruction view number. FIG. 5 shows the relationship between the acquisition view number and the reconstruction view number in the case where the number of views in which the moire artifact disappears at FOV=500 mm is 3200 views. FOV=500 mm is the maximum FOV.

The acquisition view number and the reconstruction view number at FOV=320 mm shown in FIG. 5 will be explained in detail. In the case where the size of an object is set as FOV=320 mm with respect to the maximum FOV=500 mm, the acquisition view number may be smaller than 3200 views. This is because, since the moire artifact caused by the insufficient number of views appears around the FOV, as long as the FOV=320 mm is smaller than the maximum FOV=500 mm, the moire artifact appearing around the FOV may be ignored by the user. Therefore, it is considered that the visual quality of the entire CT image will be improved by reducing the acquisition view number to less than 3200 views, and increasing the number of incident photons per view to reduce the noise artifact. For example, the acquisition view number is set to 1800 views, which is smaller than 3200 views. On the other hand, in order to reduce the moire artifact caused by the acquisition view number=1800, the number of views of the projection data immediately prior to image reconstruction is preferred to be the number of views in which the moire artifact would not appear at the maximum FOV=500 mm. Therefore, the reconstruction view number is set to 3200 views. In this case, the number of views of the projection data would be increased from 1800 views to 3200 views by the view interpolation. As mentioned above, when the number of views increased by the view interpolation is excessive, an artifact that flows in the rotational direction prominently appears. In consideration of the balance between this artifact and the moire artifact, the difference of the acquisition view number with respect to the reconstruction view number, that is, the interpolation view number, is set. As mentioned above, in the case where the FOV size is set as the examination protocol, the acquisition view number and the reconstruction view number are set so that an optimum image quality is obtained in accordance with the FOV size.

The acquisition view number and the reconstruction view number at FOV=500 mm and in a low-dose mode will be explained in the following. In the case where FOV=500 mm, the reconstruction view number is set to 3200 views in order to prevent the appearance of the moire artifact. In the case where the acquisition view number is also 3200, since the number of incident photons per view is small under the low dose, the noise artifact would be a matter of concern. Therefore, the acquisition view number is preferred to be set to a smaller view number than the reconstruction view number=3200 views. However, in the case where the acquisition view number is set too small, the artifact caused by the view interpolation becomes significant. The difference between the reconstruction view number and the acquisition view number, that is, the interpolation view number, is preferred to be set to an extent where the artifact caused by the view interpolation does not become significant. This may be set empirically. For example, the acquisition view number is set to 2500 views with respect to the reconstruction view number=3200. In other words, the acquisition view number according to the present embodiment is determined in light of the noise artifact, and not in light of the moire artifact under the low dose.

The acquisition view number and the reconstruction view number in the case where FOV=500 mm, and the image processing application is a perfusion analysis, will be explained in the following. In the case where FOV=500 mm, the reconstruction view number is set to 3200 views in order to prevent the appearance of the moire artifact. For example, in the case of a perfusion for a head or an abdomen, generally, a resolution that is as high as a normal image quality would not be required. In other words, it is assumed that an artifact caused by the view interpolation would be permissible to a certain extent. Therefore, it is preferred to actively reduce the acquisition view number, and increase the number of incident photons per view in order to reduce the noise artifact as much as possible. The amount reduced from the reconstruction view number to the acquisition view number, that is, the interpolation view number, is preferred to be set to an extent where the artifact caused by the view interpolation is permissible for the perfusion analysis. This may be set empirically. For example, the acquisition view number is set to 1500 views with respect to the reconstruction view number=3200.

The acquisition view number and the reconstruction view number in the case where FOV=500 mm, and the reconstruction method is an iterative reconstruction will be explained in the following. In the case where FOV=500 mm, the reconstruction view number is set to 3200 views in order to prevent the appearance of the moire artifact. Since the CT image reconstructed by the iterative reconstruction includes a sight blur, the moire artifact is unnoticeable. In other words, the acquisition view number should be reduced, and the number of incident photons per view should be increased in order to reduce the noise artifact. The reduced amount from the reconstruction view number to the acquisition view number should be set empirically. For example, the acquisition view number is set to 2600 views with respect to the reconstruction view number=3200.

The number of views and the reconstruction view number per examination protocol that are stored in the first view number table can be changed as needed by the user via the input circuitry 105. This allows the user to set the number of views and the reconstruction view number in accordance with the image quality the user prefers per examination protocol.

In the case where the examination protocol is set in step SA1, the processing circuitry 101 searches the first view number table based on the set examination protocol as a search key, and identifies the number of views and the reconstruction view number associated with the examination protocol. Information regarding the identified number of views is supplied to the gantry control circuitry 29.

After step SA2, the processing circuitry 101 causes the gantry control circuitry 29 to execute a CT scan (step SA3). In step SA3, the gantry control circuitry 29 controls the gantry 10 in order to acquire projection data of the acquisition view number determined in step SA2. In more detail, the gantry control circuitry 29 controls the gantry 10 in accordance with the photographing protocol included in the examination protocol set in step SA1, and executes the CT scan. The data acquisition circuitry 27 acquires the projection data of the acquisition view number determined in step SA2 via the X-ray detector 15. The acquired projection data is transmitted to the processing circuitry 101.

After step SA3, the processing circuitry 101 executes the pre-processing function 111 (step SA4). In step SA4, the processing circuitry 101 computes the projection data of the reconstruction view number by performing view interpolation based on the projection data of the acquisition view number acquired in step SA3.

After step SA4, the processing circuitry 101 executes the reconstruction function 113 (step SA5). In step SA5, the processing circuitry 101 reconstructs the CT image based on the projection data of the reconstruction view number calculated in step SA4. Specifically, the processing circuitry 101 performs reconstruction processing on the projection data of the reconstruction view number in accordance with the reconstruction protocol included in the examination protocol set in step SA1. Since the reconstructed CT image is generated based on the acquisition view number and the reconstruction view number determined in step SA2, artifacts caused by the moire artifact, the noise artifact, and the view interpolation are minimized.

After step SA5, the processing circuitry 101 causes the display 103 to perform display processing (step SA6). In step SA6, the display 103 displays the CT image that is reconstructed in step SA5. In the displayed CT image, the artifacts caused by the moire artifact, the noise artifact, and the view interpolation are minimized. This allows the user to observe a CT image with artifacts that are minimized in accordance with the examination protocol.

With the above, the explanation on the flow of the processing performed by the X-ray computed tomography apparatus under the control of the processing circuitry 101 according to Example 1 is ended.

Various changes can be applied to the above example. For example, in step SA2, the processing circuitry 101 determines the acquisition view number and the reconstruction view number by utilizing the first view number table. However, the present embodiment is not limited thereto. The processing circuitry 101 may also calculate the acquisition view number and the reconstruction view number based on a function defining the relationship between the examination protocol, the acquisition view number, and the reconstruction view number (hereinafter, referred to as a view number determination function). For example, the view number determination function corresponding to the FOV size may be defined in a manner that, as the FOV size increases, the acquisition view number decreases from the reconstruction view number.

In the above example, the view rate of the acquisition view number is assumed as being unchanged with respect to the change in the angle about the rotation axis Z of the rotation frame 11. However, the present embodiment is not limited thereto. In other words, the view rate may be changeable with respect to the change in the rotation angle. For example, it is preferable to reduce the view rate in an angle range where the number of incident photons is assumed to be insufficient, and not reduce the view rate in an angle range where the number of incident photons is not assumed to be insufficient.

For example, in the case of a photographing part in which the shape of the subject regarding an axial cross-sectional surface is flat, such as a shoulder area or a lumbar area, etc. the number of photons tend to be insufficient in an LR direction since bones are distributed in relatively large numbers in an X-ray transmission path, and the number of photons tend to be large in a PA direction. Therefore, in the case of the photographing part in which the shape of the subject regarding an axial cross-sectional surface is flat, in the first view number table, the acquisition view number is preferred to be distributed at a different rate between a first angle range and a second angle range of the rotation frame 11. The first angle range is defined as a range in which the number of incident photons does not tend to be insufficient, and the second angle range is defined as a range in which the number of incident photons tends to be insufficient. In the first angle range, a large number of views is distributed in comparison to the second angle range. For example, in the case where the photographing part is the shoulder and the lumbar, the acquisition view number is 1800, the first angle range is 315° to 45° and 135° to 225°, and the second angle range is 45° to 135° and 225° to 315°, the number of views of the first angle range is preferred to be set as 500, and the number of views of the second angle range is preferred to be set as 1300. The distribution of the reconstruction view number with respect to the first angle range and the second angle range is preferred to be set in the same numbers.

In the above manner, by making the view rate, that is, the number of views, variable in accordance with the angle range, the noise artifact caused by the insufficient number of incident photons can be further reduced while minimizing the moire artifact and the artifact caused by view interpolation.

As explained above, the X-ray computed tomography apparatus according to Example 1 includes the gantry 10, the processing circuitry 101, and the gantry control circuitry 29. The gantry 10 includes the X-ray tube 13 that generates X-rays, the X-ray detector 15 that detects the X-rays, and the data acquisition circuitry 27 that acquires projection data regarding the X-rays that are detected by the X-ray detector 15. The processing circuitry 101 includes the preprocessing function 111, the reconstruction function 113, the examination protocol setting function 117, and the view number determination function 119. The examination protocol setting function 117 sets a parameter of an examination protocol. The view number determination function 119 determines the acquisition view number of the projection data to be acquired by the CT scan and the reconstruction view number of the projection data to be utilized for image reconstruction that correspond to the set parameter. The gantry control circuitry 29 controls the gantry 10 to collect the projection data of the acquisition view number. The preprocessing function 111 calculates projection data of the reconstruction view number based on the projection data of the acquisition view number. The reconstruction function 113 reconstructs the CT image based on the projection data of the reconstruction view number.

The above configuration allows the X-ray computed tomography apparatus according to Example 1 to determine the acquisition view number and the reconstruction view number in accordance with the examination protocol, for minimizing the moire artifact caused by the insufficient number of views, the noise artifact caused by the insufficient number of incident photons, and the artifact caused by the view interpolation. In this manner, the X-ray computed tomography apparatus according to Example 1 is able to generate a CT image with an image quality optimal to the examination protocol.

Example 2

Example 2 will now be explained. Example 2 specializes in the case where a detector resolution regarding a channel direction of the X-ray detector 15 is set as an examination protocol.

Figure 6:
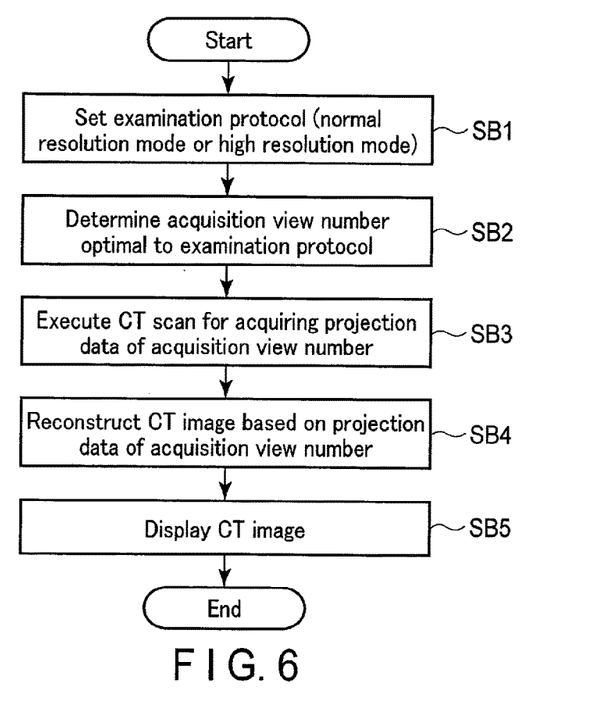
FIG. 6 is a view showing a typical flow of processing performed by the X-ray computed tomography apparatus under control of a system control function according to Example 2.

FIG. 6 is a view showing a typical flow of processing performed by the X-ray computed tomography apparatus under the control of the processing circuitry 101 according to Example 2.

As shown in FIG. 6, the processing circuitry 101 first executes the examination protocol setting function 117 (step SB1). In step SB1, the processing circuitry 101 sets the examination protocol regarding the CT scan for the subject P in accordance with an instruction from a user via the input circuitry 105, or automatically. The examination protocol according to Example 2 corresponds to either a normal resolution mode or a high-resolution mode. The parameter of the examination protocol set in Example 2 is not limited to the detector resolution, and may also be other parameters such as a rotation speed, an FOV size, an X-ray condition, an image processing application, a reconstruction method, or a reconstruction function.

After step SB1, the processing circuitry 101 executes the view number determination function 119 (step SB2). In step SB2, the processing circuitry 101 determines the acquisition view number corresponding to the examination protocol set by the examination protocol setting function 117. The processing circuitry 101 determines the acquisition view number corresponding to the examination protocol set in step SB1 based on an integrated evaluation of the moire artifact, the noise artifact, and the artifact caused by view interpolation, which flows in the rotational direction. For example, the processing circuitry 101 determines the acquisition view number by utilizing an LUT that associates the acquisition view number with each of the examination protocols regarding the detector resolution. Hereinafter, the LUT will be referred to as a second view number table. The second view number table is, for example, stored in the memory 107.

Since a pitch regarding the channel direction of the X-ray detector 15 changes between the normal resolution mode and the high-resolution mode, in the case where the same view rate is used for the normal resolution mode and the high-resolution mode, the aspects of the moire artifact and the noise artifact differ. Specifically, in the case of acquiring data at high-speed rotation in the high-resolution mode, the view rate tends to become insufficient. Therefore, in the high-resolution mode, the moire artifact appears easier than in the normal resolution mode. Furthermore, since the high-resolution mode has a smaller detection surface size than the normal resolution mode, the noise artifact caused by the insufficient number of incident photons tends to appear easier. Accordingly, for each of the normal resolution mode and the high-resolution mode, the acquisition view number is preferred to be determined in accordance with the rotation speed, the FOV size, and the SN ratio.

Figure 7:
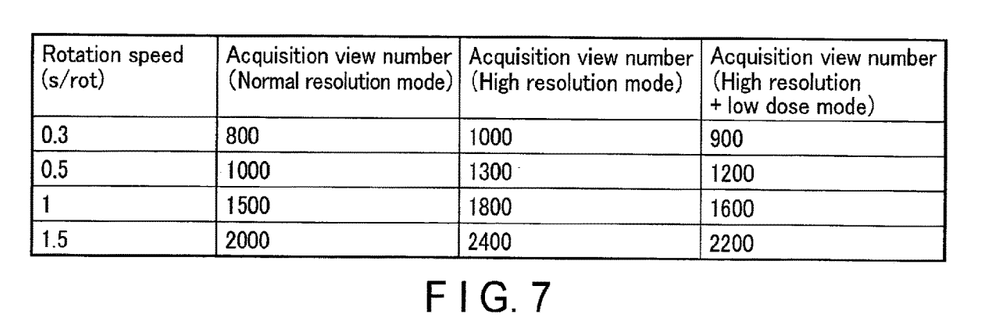
FIG. 7 shows an example of a second view number table utilized by processing circuitry in step SB2 of FIG. 6.

FIG. 7 shows an example of the second view number table utilized by the processing circuitry 101 in step SB2. As shown in FIG. 7, the second view number table associates the acquisition view number with each of the rotation speed (s/rot), the normal resolution mode, the high-resolution mode, and the high-resolution+low dose mode, which are the examination protocol. In the second view number table shown in FIG. 7, the view rate is the same for all. The high-resolution+low dose mode is a mode in which the detector resolution is high-resolution, and the X-ray dose is a low dosage.

As shown in FIG. 7, under the condition of the same view rate, the acquisition view number is set to increase as the rotation speed decreases. This is to acquire the projection data across the entire rotation angle. In the normal resolution mode, the acquisition view number is set lower than in the high-resolution mode. This is because the moire artifact is harder to appear in the normal resolution mode than in the high-resolution mode; therefore, the acquisition view number can be actively reduced to reduce the noise artifact. Since the high-resolution+low dose mode tends to have a lower number of incident photons per view in comparison to the high-resolution mode, the acquisition view number is set lower in order to increase the number of incident photons. For example, in the case where the rotation speed is 0.3 s/rot, the acquisition view number in the high-resolution mode is set to 1000, and the acquisition view number in the high-resolution+low dose mode is set to 900. In FIG. 7, although the acquisition view number in the normal resolution mode is set to a value that is smaller than the acquisition view number in the high-resolution+low dose mode, the value may be set larger than the high-resolution+low dose mode as needed.

In step SB1, in the case where the rotation speed and the detector resolution are set as the examination protocol, the second view number table is searched with a search key which is the combination of the rotation speed and the detector resolution, to identify the acquisition view number associated with the combination. Information regarding the identified acquisition view number is supplied to the gantry control circuitry 29.

In FIG. 7, the second view number table associates the detector resolution per rotation speed; however, this is not limited. For example, the second view number table may also associate the detector resolution with a parameter of the examination protocol other than the detector resolution.

After step SB2, the processing circuitry 101 causes the gantry control circuitry 29 to execute a CT scan (step SB3). In step SB3, the gantry control circuitry 29 controls the gantry 10 in order to acquire projection data of the acquisition view number determined in step SB2. In Example 2, since the acquisition view number and the reconstruction view number are the same, there is no need to execute a view interpolation.

After step SB3, the processing circuitry 101 executes the reconstruction function 113 (step SB4). In step SB4, the processing circuitry 101 reconstructs the CT image based on the projection data of the acquisition view number acquired in step SB3. Since the reconstructed CT image is generated based on the acquisition view number determined in step SB2, the moire artifact and the noise artifact are minimized.

After step SB4, the processing circuitry 101 causes the display 103 to perform display processing (step SB5). In step SB5, the display 103 displays the CT image that is reconstructed in step SB4.

With the above, the explanation on the flow of the processing performed by the X-ray computed tomography apparatus under the control of the processing circuitry 101 according to Example 2 is ended.

Various changes can be applied to the above example. For example, in the above example, the acquisition view number is determined by the second view number table, but is not limited thereto. In other words, the processing circuitry 101 may also calculate the acquisition view number based on a function that defines the relationship between the detector resolution and the parameter of the examination protocol other than the detector resolution, such as the rotation speed, the FOV size, and the SN ratio.

As explained above, the X-ray computed tomography apparatus according to Example 2 includes the gantry 10, the processing circuitry 101, and the gantry control circuitry 29. The gantry 10 includes the X-ray tube 13 that generates an X-ray, the X-ray detector 15 that is able to switch between spatial resolution modes, and the data acquisition circuitry 27 that acquires projection data regarding the X-ray that is detected by the X-ray detector 15. The processing circuitry 101 includes the reconstruction function 113, the examination protocol setting function 117, and the view number determination function 119. The examination protocol setting function 117 sets one of the spatial resolution modes of the normal resolution mode and the high-resolution mode. The view number determination function 119 determines the acquisition view number of the projection data acquired by the CT scan that corresponds to the set spatial resolution mode. The gantry control circuitry 29 controls the gantry 10 to acquire the projection data of the acquisition view number. The reconstruction function 113 reconstructs the CT image based on the projection data of the acquisition view number.

The above configuration allows the X-ray computed tomography apparatus according to Example 2 to determine the acquisition view number that minimizes the moire artifact caused by the insufficient number of views, and the noise artifact caused by the insufficient number of incident photons, in accordance with the resolution regarding the channel direction of the X-ray detector 15. In this manner, the X-ray computed tomography apparatus according to Example 2 is capable of generating a CT image with an image quality optimal to the resolution regarding the channel direction.

Since the view interpolation is not performed in the above example, the processing circuitry 101 does not determine the reconstruction view number. However, the present example is not limited thereto. In other words, in the case where the moire artifact caused by the insufficient view rate appears with the acquisition view number determined in step SB2, the view interpolation may be performed with respect to the projection data of the acquisition view number. In this case, the second view number table is preferred to associate the acquisition view number and the reconstruction view number per detector resolution in the same manner as in the first view number table of Example 1. This allows the processing circuitry 101 to determine the acquisition view number and the reconstruction view number for minimizing the moire artifact caused by the insufficient number of views, the noise artifact caused by the insufficient number of incident photons, and the artifact caused by the view interpolation, in accordance with the detector resolution.

In this case, after the processing circuitry 101 determines the acquisition view number and the reconstruction view number in step SB2, the processing circuitry 101 calculates the projection data of the reconstruction view number by performing view interpolation on the projection data of the acquisition view number in step SB3. In step SB4, the processing circuitry 101 reconstructs the CT image based on the projection data of the reconstruction view number. In this manner, even in the case where the view interpolation is performed in Example 2 where the detector resolution is changeable, a CT image with an optimal image quality in consideration of the artifact caused by the view interpolation can be reconstructed.

Therefore, according to the present embodiment, a CT image in which the reduction of artifacts, such as the moire artifact caused by the insufficient number of views and the noise artifact caused by the insufficient number of incident photons are well-balanced can be generated.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:
1. An X-ray computed tomography apparatus comprising:
processing circuitry configured to:
set a parameter of an examination protocol;

determine an acquisition view number and a reconstruction view number of projection data based on the set parameter;

acquire first projection data corresponding to the acquisition view number;

calculate second projection data corresponding to the reconstruction view number based on the first projection data; and reconstruct a CT image based on the second projection data, wherein a parameter configuring the examination protocol includes a spatial resolution regarding a channel direction of an X-ray detector, and a memory configured to store an association of an acquisition view number and a reconstruction view number per parameter of the examination protocol, wherein the processing circuitry determines the acquisition view number and the reconstruction view number that are associated with the set examination protocol.

2. The X-ray computed tomography apparatus according to claim 1, wherein the examination protocol further includes a parameter of at least one of a rotation speed of a gantry, a size of FOV, a type of post-processing for a CT image, a reconstruction method, a reconstruction function, and/or an X-ray condition.

3. The X-ray computed tomography apparatus according to claim 2, wherein, regarding the resolution, the examination protocol includes a normal-resolution mode and a high-resolution mode which has a higher resolution that the normal resolution mode.

4. The X-ray computed tomography apparatus according to claim 1, wherein the processing circuitry calculates the second projection data by performing view interpolation on the first projection data.

5. The X-ray computed tomography apparatus according to claim 1, wherein the processing circuitry determines the acquisition view number and the reconstruction view number corresponding to the set examination protocol based on an integrated evaluation of an artifact caused by an insufficient acquisition view number per unit of time, an artifact caused by an insufficient incident photon number per acquisition view, and an artifact caused by an increase from the acquisition view number to the reconstruction view number.

6. The X-ray computed tomography apparatus according to claim 1, wherein, based on the set parameter, the processing circuitry determines the reconstruction view number that has a view number different from the acquisition view number.

7. The X-ray computed tomography apparatus according to claim 1, further comprising:

a gantry that includes an X-ray tube that generates an X-ray to be irradiated on a subject, an X-ray detector that detects the X-ray transmitted through the subject, and data acquisition circuitry that acquires projection data regarding the X-ray detected by the X-ray detector, wherein the processing circuitry controls the gantry to acquire the first projection data.

8. An X-ray computed tomography apparatus comprising:
processing circuitry configured to:

set a spatial resolution mode of a first mode for acquiring projection data with a first spatial resolution, or a second mode for acquiring projection data with a second spatial resolution, which is different from the first mode;

determine an acquisition view number of the projection data based on the set spatial resolution mode; and acquire projection data of the acquisition view number, and a memory configured to store an association of each of the first mode and the second mode, and an acquisition view number, wherein the first spatial resolution and the second spatial resolution are spatial resolutions regarding a channel direction of an X-ray detector, and the processing circuitry determine the acquisition view number that is associated with the set spatial resolution modes.

9. The X-ray computed tomography apparatus according to claim 8, wherein the processing circuitry further determines a reconstruction view number based on the acquisition view number, and reconstructs a CT image based on projection data corresponding to the reconstruction view number.

10. The X-ray computed tomography apparatus according to claim 8, further comprising:

a gantry that includes an X-ray tube that generates an X-ray, an X-ray detector that is capable of switching the spatial resolution between the first mode and the second mode, and data acquisition circuitry that acquires projection data regarding the X-ray detected by the X-ray detector, wherein the processing circuitry controls the gantry to acquire the projection data of the acquisition view number regarding the set spatial resolution mode.

* * * * *